United States Patent
Friedman et al.

(10) Patent No.: US 8,081,806 B2
(45) Date of Patent: Dec. 20, 2011

(54) USER INTERFACE AND METHOD FOR DISPLAYING INFORMATION IN AN ULTRASOUND SYSTEM

(75) Inventors: Zvi Friedman, Kiryat Bialik (IL); Sergei Goldenberg, Kiryat-Ata (IL); Peter Lysyansky, Harofe st. (IL)

(73) Assignee: General Electric Company, Schenectady, NY (US)

( * ) Notice: Subject to any disclaimer, the term of this patent is extended or adjusted under 35 U.S.C. 154(b) by 1271 days.

(21) Appl. No.: 11/418,612

(22) Filed: May 5, 2006

(65) Prior Publication Data

US 2007/0258631 A1 Nov. 8, 2007

(51) Int. Cl.
*G06K 9/00* (2006.01)
*A61B 5/055* (2006.01)

(52) U.S. Cl. .......... 382/128; 382/130; 600/410

(58) Field of Classification Search .......... 382/128, 382/131; 600/424, 437, 407, 443, 447, 410
See application file for complete search history.

(56) References Cited

U.S. PATENT DOCUMENTS

| | | | |
|---|---|---|---|
| 5,709,206 A | 1/1998 | Teboul | |
| 6,099,471 A * | 8/2000 | Torp et al. | 600/438 |
| 6,546,276 B1 | 4/2003 | Zanelli | |
| 6,892,089 B1 * | 5/2005 | Prince et al. | 600/410 |
| 7,650,181 B2 * | 1/2010 | Freeman et al. | 600/510 |
| 7,657,306 B2 * | 2/2010 | Hirsh | 600/513 |
| 7,751,874 B2 * | 7/2010 | Olson | 600/512 |
| 2003/0083578 A1 * | 5/2003 | Abe et al. | 600/447 |
| 2004/0153128 A1 * | 8/2004 | Suresh et al. | 607/14 |
| 2005/0203390 A1 * | 9/2005 | Torp et al. | 600/437 |
| 2006/0004291 A1 | 1/2006 | Heimdal et al. | |
| 2006/0058592 A1 * | 3/2006 | Bouma et al. | 600/301 |
| 2006/0058673 A1 * | 3/2006 | Aase et al. | 600/450 |

FOREIGN PATENT DOCUMENTS

| | | |
|---|---|---|
| WO | WO 02/22031 A1 | 3/2002 |
| WO | WO 2006/038182 A1 | 4/2006 |

* cited by examiner

*Primary Examiner* — Vikkram Bali
*Assistant Examiner* — Nancy Bitar
(74) *Attorney, Agent, or Firm* — Dean D. Small; The Small Patent Law Group (57) ABSTRACT

A user interface and method for displaying information in an ultrasound system are provided. A medical image display of the ultrasound system includes a plurality of segmented regions each corresponding to a region of an imaged heart. The medical image display further includes a tracking quality indicator displayed in connection with one or more of the plurality of segmented regions having a tracking quality below a predetermined level.

21 Claims, 5 Drawing Sheets

USER INTERFACE AND METHOD FOR DISPLAYING INFORMATION IN AN ULTRASOUND SYSTEM

BACKGROUND OF THE INVENTION

Embodiments of the present invention relate generally to medical imaging systems, and more particularly, to medical imaging systems displaying strain information related to an imaged heart.

Ultrasound systems are used in a variety of applications and by individuals with varied levels of skill. In many examinations, operators of the ultrasound system provide inputs used by the system to process the information for later analysis. Once processed, the information may be displayed in different formats. For example, the processed information may be displayed in different charts and/or plots showing quantitative parameters or values. For example, strain values based on myocardial deformation (e.g., systolic and/or diastolic compression/expansion of the heart wall) due to cardiac ejection and/or filling may be plotted on a bullseye display. Using the bullseye display, which is typically segmented into a plurality of segments, quantitative assessment of regional myocardial function may be performed. The plurality of segments may correspond to a segmented model of the heart having radial, longitudinal and circumferential coordinates.

Local deformation may be measured to determine local contribution to ejection and/or filling based on, for example, lengthening/shortening and thickening/thinning of the heart wall and that defines a strain rate. Thus, measuring the local strain velocity provides information about the local shortening and lengthening of the heart wall. Also, determining a strain velocity provides information about the local thickening of the muscle.

The strain associated with muscle tissue generally corresponds to a ratio of the change in muscle tissue length during a time period to an initial length. In ultrasound imaging, the rate of change of strain (e.g., strain rate, strain velocity, etc.) may be visually presented to a physician as a colored segmented image, such as a bullseye plot, wherein variations in color correspond to different strain velocities. For example, strain velocity provides a direct and quantitative measure of the ability of the myocardium to contract and relax. By imaging along the myocardium from an apical view, the local strain velocity component along the long axis of the heart can be measured. By imaging from the parasternal view, the strain velocity component perpendicular to the heart wall can be determined.

Accordingly, using strain and strain rate ultrasound imaging, assessment of myocardial function may be performed. Strain measurements may be performed using different known methods to estimate cardiac deformation based on tissue deformation properties, such as tissue strain and strain velocity. However, if the determination of the strain value, for example, the tracking of the heart function is poor, such as, due to image quality (e.g., noise in the image), the calculated value may be unreliable. Thus, the display presented for review and evaluation may contain numerical values that are based on heart function tracking that is not acceptable, resulting in possible errors in evaluation and subsequent treatment.

BRIEF DESCRIPTION OF THE INVENTION

In accordance with an embodiment of the present invention, a medical image display is provided that includes a plurality of segmented regions each corresponding to a region of an imaged heart. The medical image display further includes a tracking quality indicator displayed in connection with one or more of the plurality of segmented regions having a tracking quality below a predetermined level.

In accordance with another embodiment of the present invention, a segmented plot display is provided that includes a plurality of segments each corresponding to a region of an imaged heart and forming a bullseye arrangement. Each of the plurality of segments contains therein strain information related to the imaged heart that includes at least one of numeric and color coded information. The segmented plot display further includes a plurality of global strain values displayed for average strain values for each of a plurality of imaged views of the heart.

In accordance with yet another embodiment of the present invention, a method for providing cardiac strain information on a segmented display is provided. The method includes determining whether measurement information relating to cardiac strain information is above a predetermined threshold for each of a plurality of regions of an imaged heart. The plurality of regions correspond to a plurality of segments of a segmented display. The method further includes displaying strain information in each of the plurality of segments wherein the measurement information is above the predetermined threshold.

DETAILED DESCRIPTION OF THE INVENTION

Exemplary embodiments of ultrasound systems and methods for displaying information are described in detail below. In particular, a detailed description of an exemplary ultrasound system will first be provided followed by a detailed description of various embodiments of methods and systems for displaying strain value information related to cardiac activity. A technical effect of the various embodiments of the systems and methods described herein include at least one of facilitating identification of potentially unreliable strain value information.

It should be noted that although the various embodiments may be described in connection with an ultrasound system, the methods and systems described herein are not limited to ultrasound imaging. In particular, the various embodiments may be implemented in connection with different types of medical imaging, including, for example, magnetic resonance imaging (MRI) and computed-tomography (CT) imaging. Further, the various embodiments may be implemented in other non-medical imaging systems, for example, non-destructive testing systems.

Figure 1:
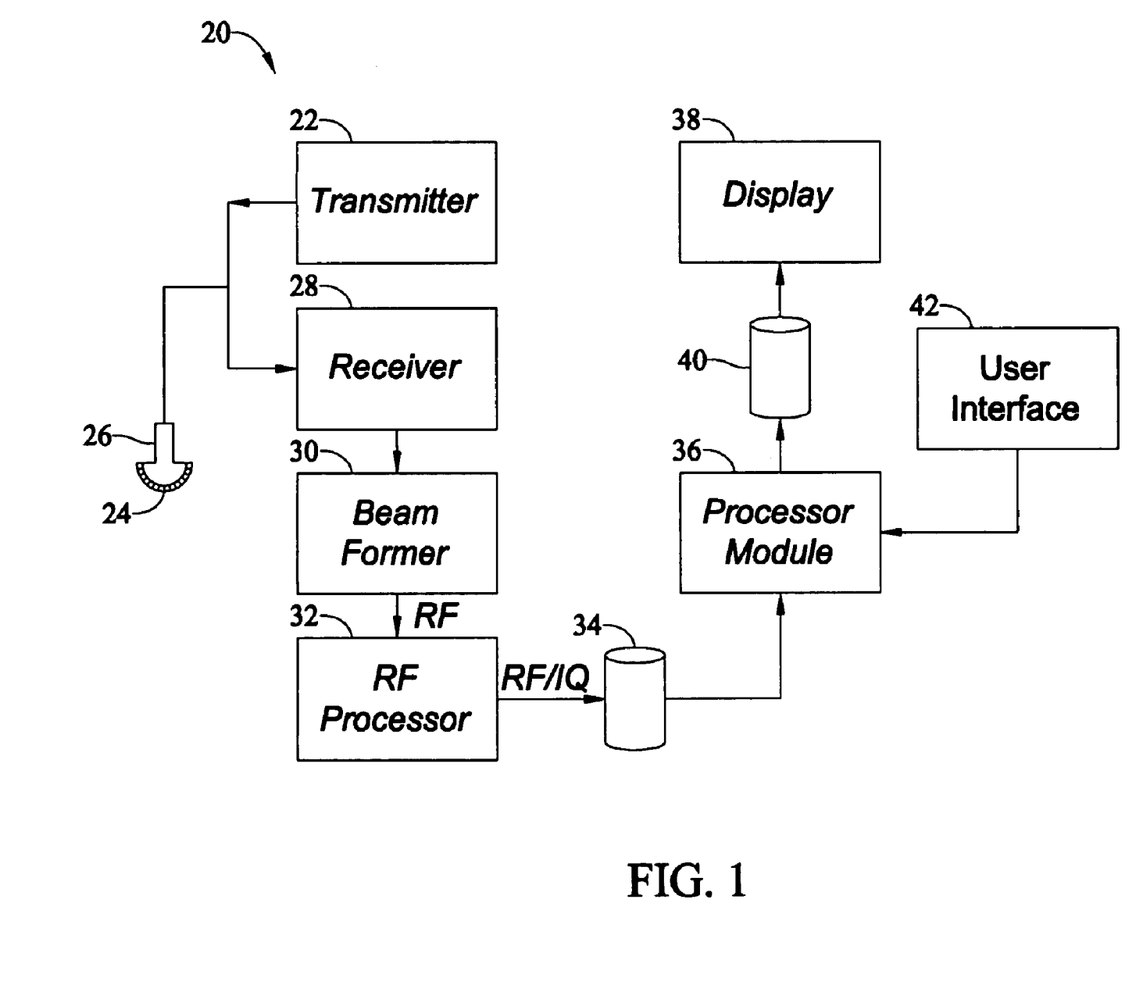
FIG. 1 is a block diagram of a diagnostic ultrasound system formed in accordance with an embodiment of the present invention.

FIG. 1 illustrates a block diagram of an ultrasound system 20, and more particularly, a diagnostic ultrasound system 20 formed in accordance with an embodiment of the present invention. The ultrasound system 20 includes a transmitter 22 that drives an array of elements 24 (e.g., piezoelectric crystals) within a transducer 26 to emit pulsed ultrasonic signals into a body or volume. A variety of geometries may be used and the transducer 26 may be provided as part of, for example, different types of ultrasound probes. The ultrasonic signals are back-scattered from structures in the body, for example, blood cells or muscular tissue, to produce echoes that return to the elements 24. The echoes are received by a receiver 28. The received echoes are provided to a beamformer 30 that performs beamforming and outputs an RF signal. The RF signal is then provided to an RF processor 32 that processes the RF signal. Alternatively, the RF processor 32 may include a complex demodulator (not shown) that demodulates the RF signal to form IQ data pairs representative of the echo signals. The RF or IQ signal data may then be provided directly to a memory 34 for storage (e.g., temporary storage).

The ultrasound system 20 also includes a processor module 36 to process the acquired ultrasound information (e.g., RF signal data or IQ data pairs) and prepare frames of ultrasound information for display on a display 38. The processor module 36 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the memory 34 during a scanning session and processed in less than real-time in a live or off-line operation. An image memory 40 is included for storing processed frames of acquired ultrasound information that are not scheduled to be displayed immediately. The image memory 40 may comprise any known data storage medium, for example, a permanent storage medium, removable storage medium, etc.

The processor module 36 is connected to a user interface 42 that controls operation of the processor module 36 as explained below in more detail and is configured to receive inputs from an operator. The display 38 includes one or more monitors that present patient information, including diagnostic ultrasound images to the user for review, diagnosis and analysis. The display 38 may automatically display, for example, multiple planes from a three-dimensional (3D) ultrasound data set stored in the memory 34 or 40. One or both of the memory 34 and the memory 40 may store 3D data sets of the ultrasound data, where such 3D data sets are accessed to present 2D and 3D images. For example, a 3D ultrasound data set may be mapped into the corresponding memory 34 or 40, as well as one or more reference planes. The processing of the data, including the data sets, is based in part on user inputs, for example, user selections received at the user interface 42.

In operation, the system 20 acquires data, for example, volumetric data sets by various techniques (e.g., 3D scanning, real-time 3D imaging, volume scanning, 2D scanning with transducers having positioning sensors, freehand scanning using a voxel correlation technique, scanning using 2D or matrix array transducers, etc.). The data is acquired by moving the transducer 26, such as along a linear or arcuate path, while scanning a region of interest (ROI). At each linear or arcuate position, the transducer 26 obtains scan planes that are stored in the memory 34.

Figure 2:
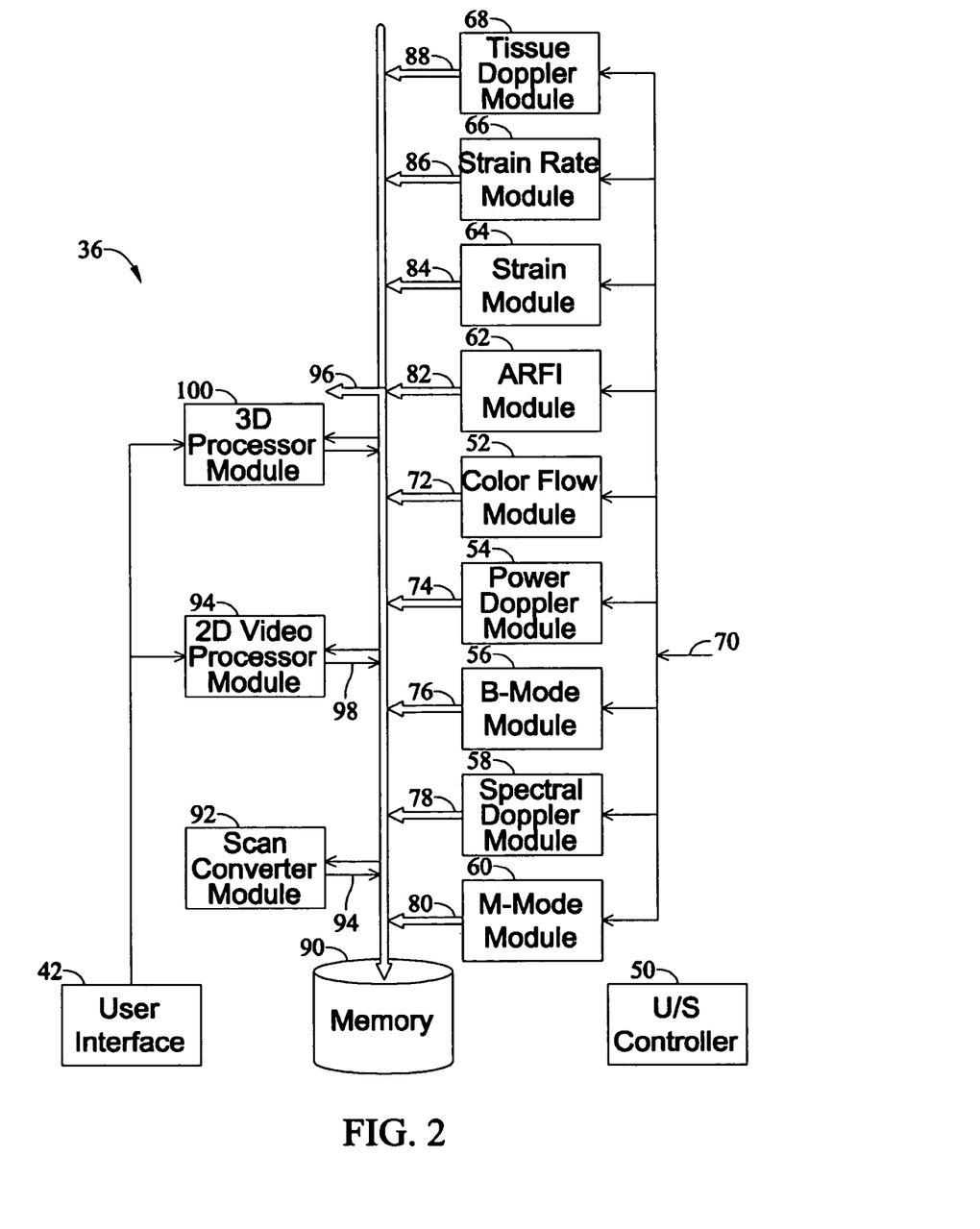
FIG. 2 is a block diagram of an ultrasound processor module of the diagnostic ultrasound system of FIG. 1 formed in accordance with an embodiment of the invention.

FIG. 2 illustrates an exemplary block diagram of the ultrasound processor module 36 of FIG. 1 formed in accordance with an embodiment of the present invention. The ultrasound processor module 36 is illustrated conceptually as a collection of sub-modules, but may be implemented utilizing any combination of dedicated hardware boards, DSPs, processors, etc. Alternatively, the sub-modules of FIG. 2 may be implemented utilizing an off-the-shelf PC with a single processor or multiple processors, with the functional operations distributed between the processors. As a further option, the sub-modules of FIG. 2 may be implemented utilizing a hybrid configuration in which certain modular functions are performed utilizing dedicated hardware, while the remaining modular functions are performed utilizing an off-the shelf PC and the like. The sub-modules also may be implemented as software modules within a processing unit.

The operations of the sub-modules illustrated in FIG. 2 may be controlled by a local ultrasound controller 50 or by the processor module 36. The sub-modules 52-68 perform mid-processor operations. The ultrasound processor module 36 may receive ultrasound data 70 in one of several forms. In the embodiment of FIG. 2, the received ultrasound data 70 constitutes I,Q data pairs representing the real and imaginary components associated with each data sample. The I,Q data pairs are provided to one or more of a color-flow sub-module 52, a power Doppler sub-module 54, a B-mode sub-module 56, a spectral Doppler sub-module 58 and an M-mode sub-module 60. Optionally, other sub-modules may be included such as an Acoustic Radiation Force Impulse (ARFI) sub-module 62, a strain module 64, a strain rate sub-module 66, a Tissue Doppler (TDE) sub-module 68, among others. The strain sub-module 62, strain rate sub-module 66 and TDE sub-module 68 together may define an echocardiographic processing portion.

Each of sub-modules 52-68 are configured to process the I,Q data pairs in a corresponding manner to generate color-flow data 72, power Doppler data 74, B-mode data 76, spectral Doppler data 78, M-mode data 80, ARFI data 82, echocardiographic strain data 82, echocardiographic strain rate data 86 and tissue Doppler data 88, all of which may be stored in a memory 90 (or memory 34 or image memory 40 shown in FIG. 1) temporarily before subsequent processing. The data 72-88 may be stored, for example, as sets of vector data values, where each set defines an individual ultrasound image frame. The vector data values are generally organized based on the polar coordinate system.

A scan converter sub-module 92 access and obtains from the memory 90 the vector data values associated with an image frame and converts the set of vector data values to Cartesian coordinates to generate an ultrasound image frame 94 formatted for display. The ultrasound image frames 94 generated by the scan converter module 92 may be provided back to the memory 90 for subsequent processing or may be provided to the memory 34 or the image memory 40.

Once the scan converter sub-module 92 generates the ultrasound image frames 94 associated with, for example, the strain data, strain rate data, and the like, the image frames may be restored in the memory 90 or communicated over a bus 96 to a database (not shown), the memory 34, the image memory 40 and/or to other processors (not shown).

As an example, it may be desired to view different types of ultrasound images relating to echocardiographic functions in real-time on the display 38 (shown in FIG. 1). To do so, the scan converter sub-module 92 obtains strain or strain rate vector data sets for images stored in the memory 90. The vector data is interpolated where necessary and converted into an X,Y format for video display to produce ultrasound image frames. The scan converted ultrasound image frames are provided to a display controller (not shown) that may include a video processor that maps the video to a grey-scale mapping for video display. The grey-scale map may represent a transfer function of the raw image data to displayed grey levels. Once the video data is mapped to the grey-scale values, the display controller controls the display 38, which may include one or more monitors or windows of the display, to display the image frame. The echocardiographic image displayed in the display 38 is produced from an image frame of data in which each datum indicates the intensity or brightness of a respective pixel in the display. In this example, the display image represents muscle motion in a region of interest being imaged.

Referring again to FIG. 2, a 2D video processor sub-module 94 combines one or more of the frames generated from the different types of ultrasound information. For example, the 2D video processor sub-module 94 may combine a different image frames by mapping one type of data to a grey map and mapping the other type of data to a color map for video display. In the final displayed image, the color pixel data is superimposed on the grey scale pixel data to form a single multi-mode image frame 98 that is again re-stored in the memory 90 or communicated over the bus 96. Successive frames of images may be stored as a cine loop in the memory 90 or memory 40 (shown in FIG. 1). The cine loop represents a first in, first out circular image buffer to capture image data that is displayed in real-time to the user. The user may freeze the cine loop by entering a freeze command at the user interface 42. The user interface 42 may include, for example, a keyboard and mouse and all other input controls associated with inputting information into the ultrasound system 20 (shown in FIG. 1).

A 3D processor sub-module 100 is also controlled by the user interface 42 and accesses the memory 90 to obtain spatially consecutive groups of ultrasound image frames and to generate three dimensional image representations thereof, such as through volume rendering or surface rendering algorithms as are known. The three dimensional images may be generated utilizing various imaging techniques, such as ray-casting, maximum intensity pixel projection and the like.

Figure 3:
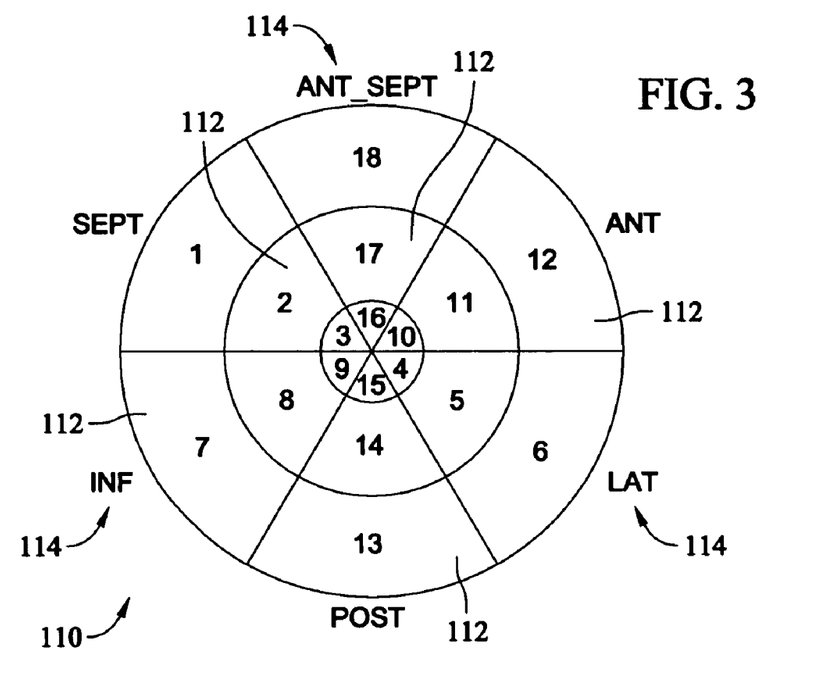
FIG. 3 illustrates a segmented display in connection with which various embodiments of the invention may be implemented.
Figure 4:
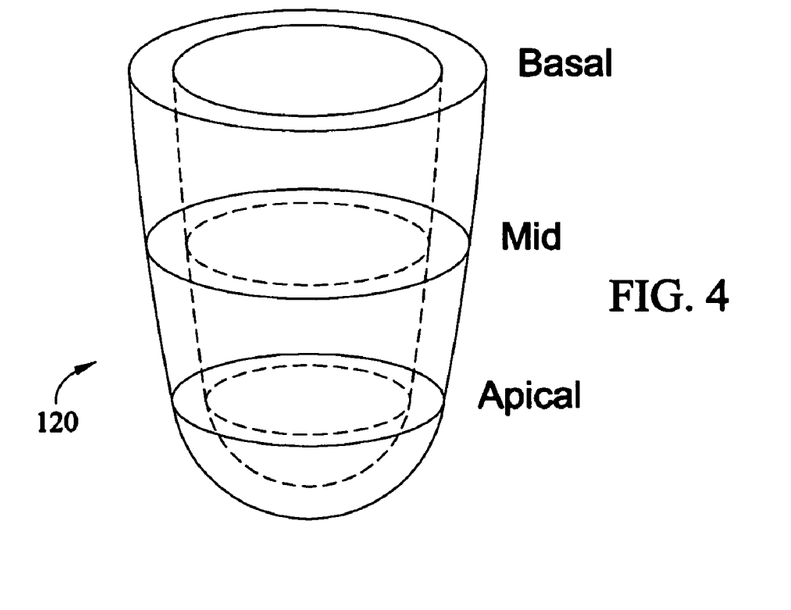
FIG. 4 is a perspective view of a segmented model of a heart corresponding to the segmented display of FIG. 3.

Various embodiments of the present invention display strain information calculated from measured cardiac activity and provide an indication on a display of the reliability of the strain information. In particular, a segmented display 110 as shown in FIG. 3 is provided and may be configured in a bullseye arrangement. For example, the segmented display 110 generally includes a plurality of segments 112 forming segmented areas or regions and together defining a circular display that may be configured as a parametric display of the entire myocardial surface of a heart. The parametric display may be generated in any known manner, for example, by interpolation of peak systolic values along a myocardial wall of a heart acquired and processed in different views, such as three standard apical views (apical long axis (APLAX), four chamber and two chamber). It should be noted that the segmented display 110 may be modified to include a different number of segments 112, for example, seventeen or sixteen segments. The number of segments 112 generally may be more than or less than the eighteen segments shown and may be based on a segmented model 120 of a heart, for example, as shown in FIG. 4.

Position labels 114 also may be provided to indicate the location/orientation from which the displayed information was acquired (e.g., posterior (POS), anterior (ANT), etc.) based on the segmented model 120. The position labels 114 are generally associated with a different slice of the segmented display. The order of the segments 114 are numerically identified in FIG. 3, for example, using any known or conventional/standard numbering and ordering, for example, with the segments 114 numbered and representing various heart segments (e.g., apical, mid and basal) along the corresponding wall (e.g., septal, lateral, anterior, posterior, etc.). However, the arrangement, positioning and ordering of the segments 114 may be modified as desired or needed.

In general, the segmented display 110 displays quantitative parameters derived from measured strain of cardiac activity. For example, each of the segments 112 may be numerically and/or graphically labeled to show the associated strain derived parameters, which in one embodiment is peak systolic strain. The calculated strain measured from tissue deformation may be determined in any known manner, for example, by determining a velocity field for each segmented region based on tracking structures in the heart from one image frame to the next. Local velocities may be determined, for example, from maps of the frames. One example of a method for calculating tissue deformation using ultrasound imaging is described in U.S. Pat. No. 6,352,507 entitled "METHOD AND APPARATUS FOR PROVIDING REAL-TIME CALCULATION AND DISPLAY OF TISSUE DEFORMATION IN ULTRASOUND IMAGING."

Figure 5:
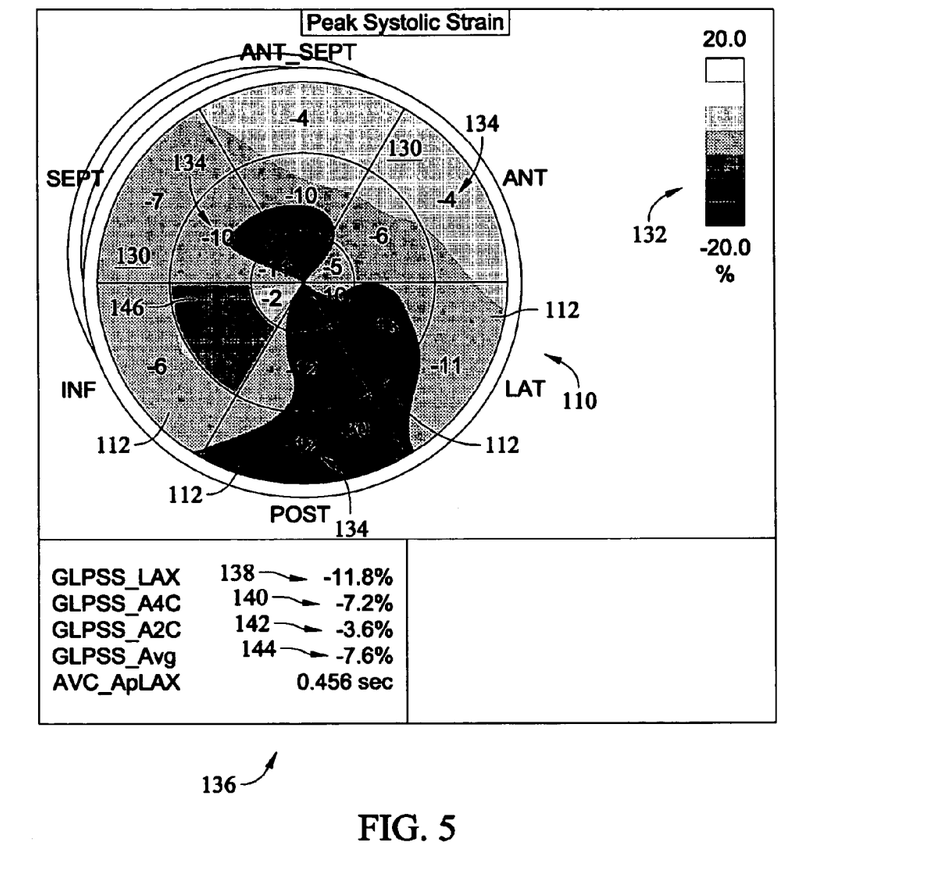
FIG. 5 is a display window having a segmented display formed in accordance with an embodiment of the invention.

The segmented display 110 may be presented on a screen or a portion thereof (e.g., a window) of the display 38 (shown in FIG. 1). Specifically, as shown in FIG. 5, the segmented display 110 may be displayed having color coded regions 130 defining areas within the segmented display 110 having strain values corresponding to a range as defined by a strain level legend 132. The strain level legend 132 may be, for example, a continuous scale defining a range of peak systolic wall thickening percentages. The various parameters may be plotted, for example, with respect to different stress levels and the color coded regions 130 may extend into more than segment 112 or may be contained in a single segment 112. The color coded regions 130 are displayed independent of the boundaries of the segments 112 and may traverse one or more boundaries. Additionally, a strain value 134 is displayed within each segment 112 and corresponds to the calculated average peak systolic strain for that segment 112.

Further, average strain information 136 may be displayed on the screen, for example, in a separate window or portion of the screen. The average strain information 136 may include strain values averaged over different regions of the heart or for different views. For example, the average strain value for the entire myocardial wall may be provided separately for each of a plurality of views, such as, global peak systolic strain (GLPSS) values including an APLAX average strain value 138 (GLPSS_LAX), an apical four chamber average strain value 140 (GLPSS_A4C), an apical two chamber average strain value 142 (GLPSS_A2C) and an overall strain value 144 (GLPSS_Avg) representing the average strain over the entire myocardial wall.

The segmented display 110 is also provided such that segments 112 in which the calculated strain value is determined to include errors or that insufficient information exists to acquire accurate measurements resulting in possible unreliable data are indicated as having tracking information below a predetermined level, for example, below an acceptable or poor tracking level. This determination may be based on any of a plurality of factors, including, for example, image quality, image noise, etc. The segments 112 having calculated strain values that are based on acquired data that is below the predetermined level are marked accordingly, for example, by providing a tracking quality indicator, for example, a mask, such as a gray fill area 146 in that segment 112. Further, the strain value 134 is not displayed in that segment 112. Thus, the gray fill areas 146 define segments 112 wherein tracking quality or other processes used to acquire strain data is below a predetermined level, such as an acceptable level, below which acquired strain information may be inaccurate.

It should be noted that the gray fill area 146 may be provided in more than one segment 112 that may be adjacent to or separated by other segments 112. In the various embodiments, when a single gray fill area 146 is provided, the average strain information 136 continues to be displayed. When the number of gray fill areas 146 exceeds a predetermined number, for example, two, then the average strain information 136 is no longer displayed.

Figure 6:
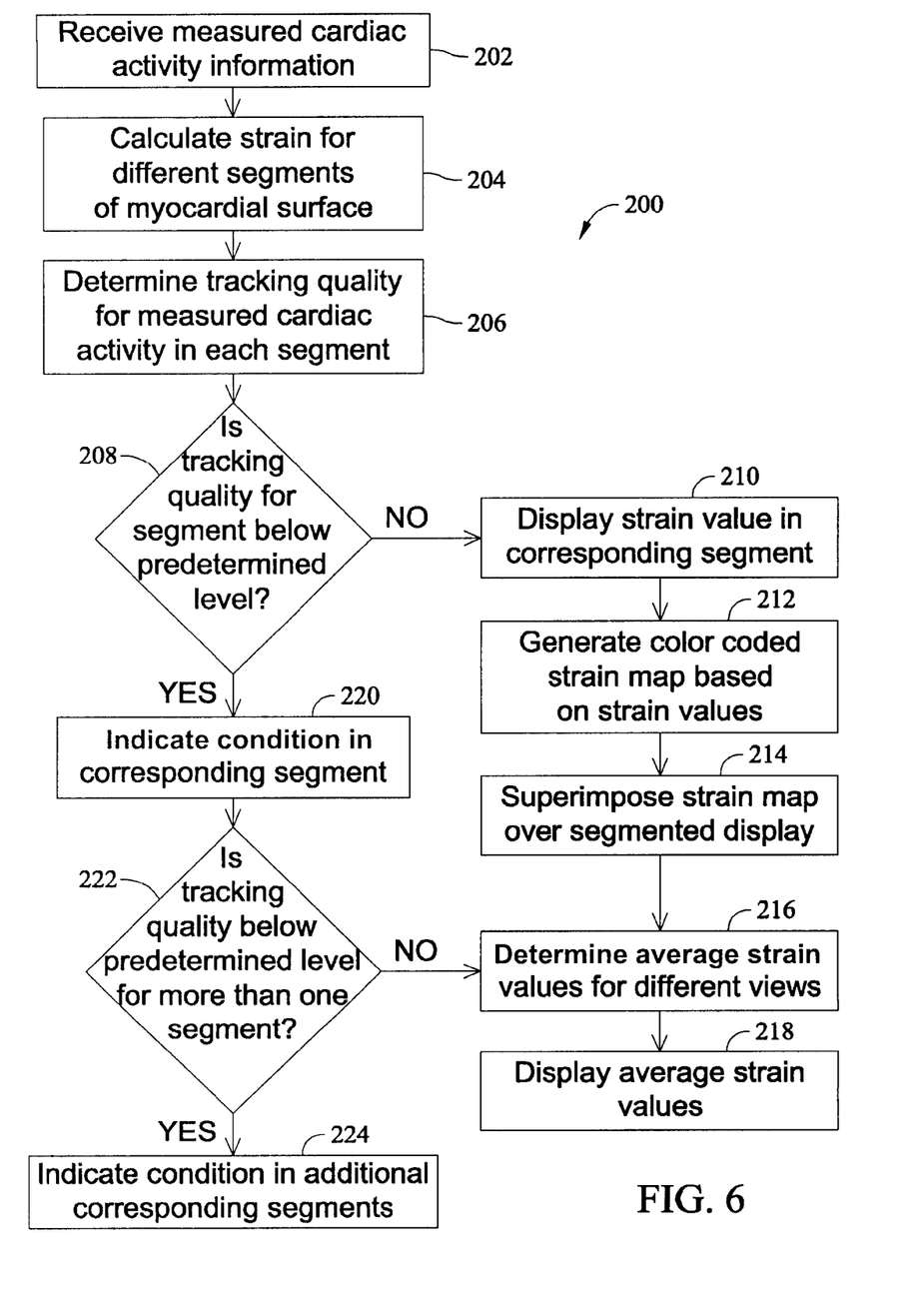
FIG. 6 is flowchart of a method in accordance with an embodiment of the invention to display cardiac strain information on a segmented display.

Various embodiments provide a method 200 as shown in FIG. 6 to display cardiac strain information on a segmented display, for example, on a display of an ultrasound system. Specifically, at 202 measured cardiac activity information is received. For example, peak systolic values along a myocardial wall of a heart are received. The peak systolic values may be obtained by any known method, for example, using tissue velocity imaging or strain rate imaging to obtain different tissue deformation parameters (e.g., expansion/contraction and/or lengthening/shortening). The cardiac activity may be acquired by sampling several image frames (e.g., several consecutive frames) to determine a strain rate estimate over a certain time period. Essentially, a tracking function may be performed to measure different characteristics (e.g., track structures) from frame to frame. This tracking may include, for example, measuring velocity fields generated by frame to frame tracking to obtain strain values. Thereafter at 204 strain values for different segments of the myocardial surface, for example, along the myocardial wall are calculated. This may include processing the acquired peak systolic values in different views, such as three standard apical views (apical long axis (APLAX), four chamber and two chamber).

The tracking quality for the measured cardiac activity for each segment is then determined at 206. This process generally involves determining a confidence level, for example, a predetermined acceptable level, at which the acquired data may be used and considered reliable. A determination may be made as to the image quality of the frames used for tracking. For example, the noise level for the frames may be determined and compared to a threshold acceptable level of noise. However, tracking quality may be measured using any method for determining whether the acquired data is reliable based on a defined setting. As another, example, the variance of velocities in a measured area may be evaluated. For example, the calculated velocity fields for adjacent points in an area may be compared to determine a variance. A threshold variance difference may be set above which the acquired data is determined to be not reliable or acceptable. As another tracking method, a coordinate within an area may be tracked to determine if when moving back and forth between image frames that coordinate corresponds to the same point. An acceptable variance may again be set.

Thereafter at 208 a determination is made as to whether the tracking quality for a segment (e.g., one of the segments of the segmented display) is below a predetermined level, namely that the quality is determined to be not acceptable or not reliable because the tracking quality does not meet the predetermined level. For example, the different thresholds described above to determine tracking quality may be used. If the tracking quality is not below the predetermined threshold, then at 210 the determined strain values, for example, peak systolic strain values are displayed. For example, the strain value 134 may be displayed within each segment 112 of the segmented display 110 and corresponds to the calculated peak systolic strain for that segment 112 (all shown in FIG. 5). A color coded strain map also is generated at 212 based on the calculated strain values. For example, the calculated strain values may be stored in a database associating the strain value with a coordinate of the model of the heart (as shown in FIG. 4) or a particular pixel of the imaged heart. These strain values then may be used to generate a color coded strain map. The map may be generated using any known method. The color coded strain map is then superimposed, for example, over the segmented display 110. The coloring of the display is based on the defined locations within the segmented display 110, for example, based on the orientation of the various segments 112 and the corresponding portion of the heart to which that segment 112 relates.

The average strain values for different views are then determined at 216. For example, global strain values equivalent to the average strain over the entire myocardial wall are determined for each of a plurality of views. Any averaging technique may be used to determine an average of the measured strain values. The average strain values are then displayed at 218, for example, in a window separate from the segmented display 110.

Referring again to the determination at 208 of whether the tracking quality for a segment is below a predetermined level, if the tracking quality is below the predetermined level, then at 220, the unacceptable tracking quality condition is indicated on the display. For example, in one embodiment, the segment 112 having the tracking level below the predetermined level is provided with a mask, for example, a gray fill area 146 (shown in FIG. 5), such that no mapping or value information is displayed in the segment 112. A determination is also made at 222 as to whether the tracking quality is below the predetermined threshold for more than one segment. If the tracking quality for more than one segment is below the predetermined level, then the condition is indicated at 224, for example, in the additional segments 112 by the gray fill area 146. Additionally, average strain values for different views are not calculated and displayed. If the tracking quality is not below the predetermined level for more than one segment, then the average strain values for different views is determined and displayed at 216 and 218, respectively.

It should be noted that peak systolic strain is just one example of a functional (PSS=F{S($t_i$)}) of all strain values within the heart cycle. In the various embodiments, different and/or additional functionals may be computed for each myocardial position, and a multi-color scheme can be used to represent the different and/or additional functionals.

Thus, various embodiments of the present invention provide a segmented display providing strain information and an indication of whether strain values are at an acceptable quality level (e.g., acceptable tracking level). The segmented display also may provide a color coded strain map extending through different segments of the segmented display. Overall average values of strain also may be displayed.

While the invention has been described in terms of various specific embodiments, those skilled in the art will recognize that the various embodiments of the invention can be practiced with modification within the spirit and scope of the claims.

What is claimed is:

1. A medical image display comprising:
a plurality of segmented regions each corresponding to a region of an imaged heart; and
a tracking quality indicator displayed in connection with one or more of the plurality of segmented regions having a tracking quality below a predetermined level, wherein the tracking quality indicator corresponds to a determined quality of tracking for a plurality of frames of image data corresponding to the region of the imaged heart and comprises a mask defining a fill area configured to cover the one or more segmented regions having a tracking quality below the predetermined level.

2. A medical image display in accordance with claim 1 wherein the fill area encompasses the one or more segments and conceals strain information contained therein.

3. A medical image display in accordance with claim 1 wherein tracking quality comprises a noise level of an acquired image.

4. A medical image display in accordance with claim 1 wherein tracking quality comprises a velocity field variance of acquired data.

5. A medical image display in accordance with claim 1 further comprising a color coded strain map superimposed over the plurality of segments.

6. A medical image display in accordance with claim 5 wherein the color coded strain map comprises color coded regions defining areas having strain values corresponding to a strain value range.

7. A medical image display in accordance with claim 6 wherein the color coded regions traverse more than one of the plurality of segmented regions.

8. A medical image display in accordance with claim 1 further comprising average strain values displayed for each of a plurality of views of the imaged heart.

9. A medical image display in accordance with claim 8 wherein the average strain values are not displayed if more than one of the plurality of segmented regions has a tracking quality below the predetermined level.

10. A medical image display in accordance with claim 1 further comprising peak systolic strain information displayed in each of the plurality of segmented regions.

11. A medical image display in accordance with claim 1 wherein the plurality of segmented regions define a bullseye arrangement.

12. A segmented plot display comprising:
a plurality of segments each corresponding to a region of an imaged heart and forming a bullseye arrangement, each of the plurality of segments containing therein strain information related to the imaged heart including at least one of numeric and color coded information;
a plurality of global strain values displayed for average strain values for each of a plurality of imaged views of the heart; and
a mask encompassing at least one of the plurality of segments wherein the strain information contained therein is determined to be not reliable based on an analysis of a tracking quality for a plurality of image frames corresponding to the region of the imaged heart, such that the strain information is not viewable in the masked segment and the global strain values are not displayed if more than one of the plurality of segments is masked.

13. A segmented plot display in accordance with claim 12 wherein the color coded information comprises color coded regions traversing at least one boundary between two of the plurality of segments.

14. A method for providing cardiac strain information on a segmented display, the method comprising:
determining whether measurement information relating to cardiac strain information is above a predetermined threshold for tracking quality for each of a plurality of regions of an imaged heart, the plurality of regions corresponding to a plurality of segments of a segmented display and wherein the tracking quality is based on an analysis of a plurality of frames of image data used to track heart function for determining the cardiac strain information;
displaying strain information in each of the plurality of segments wherein the measurement information is above the predetermined threshold; and
displaying global strain information if a predetermined number of the plurality of segments include measurement information below the predetermined threshold.

15. A method in accordance with claim 14 wherein the strain information comprises at least one of strain value information and color coded strain mapping information.

16. A method in accordance with claim 14 further comprising displaying global strain information if less than two of the plurality of segments include measurement information below the predetermined threshold.

17. A method in accordance with claim 14 further comprising displaying color coded strain mapping information across boundaries of the plurality of segments.

18. A medical image display in accordance with claim 1 wherein the predetermined level defines a reliable quality tracking level and wherein the tracking quality indicator is determined for all of the plurality of frames of image data to identify segments having data that is determined to be not reliable.

19. A medical image display in accordance with claim 1 wherein the plurality of frames of image data correspond to acquired image data for the region of the imaged heart and wherein the tracking quality indicator is determined based on an image quality for the plurality of frames of image data.

20. A medical image display in accordance with claim 1 wherein the plurality of frames of image data correspond to acquired image data for the region of the imaged heart and wherein the tracking quality indicator is determined based on a variance in calculated velocity fields in a measured area for the plurality of frames of image data.

21. A segmented plot display in accordance with claim 12 wherein the mask covers the entire segment defining a fill area displayed as a solid color.

* * * * *